(12) United States Patent
Stähler et al.

(10) Patent No.: US 7,320,862 B2
(45) Date of Patent: Jan. 22, 2008

(54) MICROFLUIDIC EXTRACTION METHOD

(76) Inventors: Cord F. Stähler, Gässelweg 15, 69469 Weinheim (DE); Peer F. Stähler, Obere Clignetstrasse 14, 68167 Mannheim (DE); Manfred Müller, Mannheimerstrasse 11, 69198 Schriesheim (DE)

( * ) Notice: Subject to any disclaimer, the term of this patent is extended or adjusted under 35 U.S.C. 154(b) by 282 days.

(21) Appl. No.: 10/492,014

(22) PCT Filed: Oct. 10, 2002

(86) PCT No.: PCT/EP02/11383

§ 371 (c)(1),
(2), (4) Date: Oct. 13, 2004

(87) PCT Pub. No.: WO03/031965

PCT Pub. Date: Apr. 17, 2003

(65) Prior Publication Data

US 2005/0040043 A1  Feb. 24, 2005

(30) Foreign Application Priority Data

Oct. 10, 2001  (DE) .............................. 101 49 947

(51) Int. Cl.
*C12Q 1/68* (2006.01)
*G01N 33/53* (2006.01)
*C07H 21/02* (2006.01)
*C07H 21/04* (2006.01)

(52) U.S. Cl. .......................... 435/6; 435/7.1; 536/23.1; 536/24.3

(58) Field of Classification Search ..................... 435/6, 435/7.1; 536/23.1, 24.3; 530/350
See application file for complete search history.

(56) References Cited

U.S. PATENT DOCUMENTS 5,985,563 A * 11/1999 Hyldig-Nielsen et al. ...... 435/6
5,985,651 A * 11/1999 Hunicke-Smith ........ 435/285.1
6,596,487 B2 * 7/2003 Raees et al. .................... 435/6
6,953,686 B1 * 10/2005 Ramasubramanyan ... 435/288.6
2005/0009020 A1   1/2005 Distler

FOREIGN PATENT DOCUMENTS

| EP | 0 846 776 A | | 6/1998 |
| WO | WO 00/49142 | * | 8/2000 |
| WO | WO 01 40509 A | | 6/2001 |
| WO | WO 02 12855 A | | 2/2002 |
| WO | WO 02 052045 A | | 7/2002 |
| WO | WO 02 083943 A | | 10/2002 |

OTHER PUBLICATIONS

Piette, J. et al. , "Production of Breaks in Single- and Double-Stranded Forms of Bacteriophage .PHI.X174 DNA by Proflavine and Light Treatment," Photochemistry and Photobiology 30:369-378(1979).*
Ericson et al., "Electroosmosis-and Pressure-Drivin Chromatography in Chips using Continuous Beds", Analytical Chemistry, vol. 72, No. 1, Jan. 1, 2000, pp. 81-87.
Bing He et al., "Microfabricated liquid chromatography columns base on collocated monolith support structures", Journal of Pharmaceutical and Biomedical Analysis, vol. 17, Sep. 1, 1998, pp. 925-932.
Jörg et al., "Solvent-Programmed Microchip Open-Channel Electrochromatography", Analytical Chemistry, vol. 70, Aug. 1, 1998, pp. 3291-3297.
Bruin, "Recent Developments in Electrokinetically Driven Analysis on Microfabricated Devices", ELECTROPHORESIS, vol. 21, 2000, pp. 3931-3951.
Ge, Hui, "UPA, a Universal Protein Array System For Quantitative Detection of Protein-Protein, Protein-DNA, Protein-RNA and Protein-Ligand Interactions," Nucleic Acids Research, 28(2):i-vii, 2000.

* cited by examiner

*Primary Examiner*—Ethan Whisenant
(74) *Attorney, Agent, or Firm*—Rothwell, Figg, Ernst & Manbeck pc

(57) ABSTRACT

The invention relates to an extraction method for isolating target molecules from a sample using a microfluidic carrier.

30 Claims, 2 Drawing Sheets

Figure 2
Figure 2A
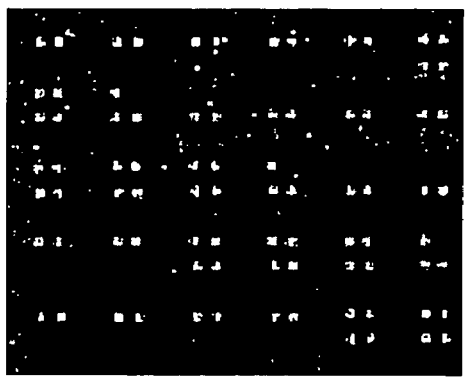
Figure 2B
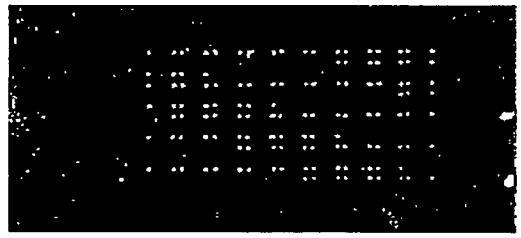

MICROFLUIDIC EXTRACTION METHOD

CROSS REFERENCE TO RELATED APPLICATION

This application is a 35 USC § 371 National Phase Entry Application from PCT/EPO2/11383, filed Oct. 10, 2002, and designating the U.S.

The invention relates to an extraction method for isolating target molecules from a sample using a micro-fluidic carrier.

The selective extraction of molecules is a central and important process for many fields of work in biochemistry, biology and medicine. These fields of work include extraction and purification of nucleic acids, proteins, sugars and other biochemical functional molecules.

In genetics too, biochemical methods for extracting particular molecules, compounds or substance classes play an important part. Particularly important here is the purification of nucleic acids, usually DNA and RNA. Essential steps in recombination technology require isolation and purification of particular nucleic acids, for example of plasmid DNA. The construction of gene libraries from messenger RNA (mRNA), which is of central importance in genetic engineering, depends on isolation of a desired RNA population. Genes or gene fragments are "fished" from such libraries in order to be able to further study or manipulate them.

The efficiency and meaningfulness of biochemical, biological and medical analytic methods can be enormously increased by miniaturization and parallelization. Such miniaturizations relate, for example, to the analysis of genetic material with the aid of hybridization experiments on DNA microarrays. The development of microarrays of suitable DNA probes as receptors enables entire genomes and transcriptomes to be analyzed. Extraction methods play an important part in the preparation and application of microarrays and are, at the same time, an important cost factor, where those microarrays are concerned for which the corresponding polymeric DNA probes are synthesized independently of the reaction carrier ("off chip" synthesis) and then applied to said reaction carrier. Aside from the quite widespread DNA microarrays, methods which serve the screening for molecules with particular properties, for example ribozymes, have also been miniaturized and parallelized. Further examples of receptors on microarrays are proteins and those molecules which do not naturally occur, such as peptide nucleic acids (PNA), for example. Many of those assay formats are listed under the category biochips. The isolation and purification of the sample material are central processes of sample preparation for virtually all of these assay formats.

Microreaction techniques may be coupled to microarrays of this kind in order to achieve rapid and efficient systems both for sample preparation and for preparation of the actual array. This also includes the use of microfluidic methods.

Numerous methods for biochemical isolation of nucleic acids are available. Although said methods allow RNA or DNA to be isolated and, where appropriate, also purified via its biophysical properties, they are totally unspecific with respect to the sequence of the nucleic acid strand.

Thus it is possible to isolate relatively specifically mRNA molecules from total RNA comprising different types of RNA by immobilizing polythymidine strands (poly-T strands) on a solid phase, for example latex beads, magnetic beads, controlled pore glass beads or a column matrix. After addition of total RNA, said poly-T strands hybridize with the polyadenine (poly-A) tail of mRNA molecules and allow the unbound RNA molecules to be removed. The mRNA molecules are then isolated by changing the buffer appropriately so as to stop hybridization in favor of single strands. The liberated mRNA molecules can then be eluted.

The amount of information in an isolation matrix of this kind is comparatively low, since only two categories of target molecules can be distinguished, namely those with and without poly-A tail.

A similar situation usually exists in the case of methods for isolating proteins. Thus, immunoglobulins are often isolated using an isolation matrix in a column containing immobilized protein A (from Staphylococcus aureus) (Brown et al., Biochem. Soc. Transactions (England) 26 (1998), 249). In other versions of said method, antibodies for one or a few target molecules are bound to the isolation matrix.

Isolation methods of this kind are generally referred to as affinity chromatography. A disadvantage of these methods is the fact that parallel selective isolation of different target molecules is not possible.

U.S. Pat. No. 6,013,440 describes a method for preparing an affinity matrix, which comprises immobilizing a set of different nucleic acid probes on a solid carrier, in order to concentrate in this way target nucleic acids of a still unknown sequence from a sample. Besides other disadvantages, it should be mentioned that the isolation matrix used in the proposed method is two-dimensional carriers which allow only inconvenient elution. This method too, is thus incapable of removing the disadvantages known from the prior art.

The present invention provides a method and an apparatus which use as isolation matrix a microfluidic carrier which allows selective isolation of particular biochemical functional molecules (target molecules), in particular selective parallel isolation of several species of target molecules, from a mixture. The method comprises selective isolation of biochemically functional target molecules by binding to a substrate with immobilized receptors as interaction partners. The functionality of a target molecule is defined by its ability to selectively bind to a receptor specific for said target molecule, preferably via bioaffinity interactions, such as hybridization, receptor-ligand binding, antigen-antibody binding, saccharide-lectin binding, etc.

For this purpose, the method of the invention makes use of providing a microfluidic carrier having an array of selectively binding receptors or capture probes as isolation matrix for the target molecules. In a preferred embodiment, the receptors are synthesized in situ on or in the microfluidic reaction carrier. This procedure for preparing the isolation matrix allows the latter to contain a very large amount of information when appropriate methods for in situ synthesis are used. In the case of nucleic acids as target molecules, a suitable system for in situ synthesis of the corresponding capture probes can produce thousands of defined sequences on the isolation matrix. Thus, the invention opens a route for specifically extracting specifically hundreds to thousands of individual DNA or RNA molecules from a mixture.

The carrier comprising the immobilized receptors may be employed, for example, in academic research, basic research, industrial research, in quality control, in pharmaceutical research, in biotechnology, in clinical research, in clinical diagnostics, in screening methods, in diagnostics of individual patients, in clinical studies, in forensics, for genetic tests such as parenthood determinations, in animal breeding and plant cultivation or in environmental monitoring.

The invention thus relates to a method for isolating target molecules from a sample, comprising the following steps:

(a) providing a microfluidic carrier having an array of a plurality of different freely selectable receptors which are immobilized on or in the carrier on in each case different positions,
(b) directing a sample comprising target molecules to be isolated through said microfluidic carrier under conditions under which target molecules can specifically bind to the receptors immobilized on the carrier,
(c) removing unbound material of the sample from the carrier, and
(d) eluting the target molecules bound to the carrier.

The target molecules isolated by the method of the invention are preferably selected from biological polymers such as nucleic acids, for example double-stranded or single-stranded DNA molecules, for example genomic DNA molecules or cDNA molecules, or RNA molecules, polypeptides such as, for example, proteins, glycoproteins, lipoproteins, nucleoproteins, etc., peptides and saccharides.

The target molecules are preferably nucleic acids and the receptors on the microfluidic carrier are selected from hybridization probes complimentary thereto. Said hybridization probes may likewise be nucleic acids, in particular DNA molecules, but may also be nucleic acid analogs such as peptide nucleic acids (PNA), locked nucleic acids (LNA), etc. The length of the hybridization probes preferably corresponds to 10-100 nucleotides and said hybridization probes need not entirely consist of building blocks with bases, i.e. they may also contain, for example, abasic building blocks, linkers, spacers, etc. The hybridization probes may be bound to the carrier at the 3' end, the 5' end or in between or in multiple positions.

The receptors may be immobilized on the microfluidic carrier by noncovalent or covalent interactions. Preference is given to carrying out covalent immobilization, particularly preferably via bi- or polyfunctional spacer molecules. Alternatively, preference is given to immobilization via electrostatic interactions or bioaffinity interactions, for example streptavidin/biotin, avidin/biotin, etc.

Another preferred example of receptors are peptides. In addition, it is, of course, also possible to use libraries of low molecular weight substances as receptors.

The receptors immobilized on the carrier, for example hybridization probes, are preferably generated on the carrier by in situ synthesis, for example by step-by-step construction of synthetic building blocks, and are thus freely selectable. The building blocks for said in situ synthesis may be monomers of the substance class in question, i.e. nucleotide building blocks, for example, in the case of nucleic acids. However, they may also be more complex building blocks, thus, for example, oligonucleotides or oligopeptides composed of several, for example 2, 3 or 4, monomeric units.

The sample used for the method of the invention is preferably a complex sample, i.e. the target molecules must be selectively isolated from a multiplicity of similar molecular species. The sample may be a biological sample, for example a sample from a biological organism, for example from a body fluid, a sample from a cell culture or a culture of micro-organisms, etc. The sample may furthermore also come from synthetic sources, for example from a synthesis apparatus, or may be a mixture of biological and synthetic material.

The sample may, where appropriate, be processed prior to application to the carrier, for example by enzymic reaction such as amplification, restriction cleavage, labeling, transcription, translation, fractionation, preliminary purification, etc. The target molecules to be isolated may thus be present in a labeled or unlabeled form.

The method of the invention is preferably carried out on structured carriers, particularly preferably on carriers with channels, for example with closed channels. Examples of said channels are microchannels having a 10-10 000 μm cross section. Examples of suitable carriers with channels are described in WO 00/13017 and WO 00/13018. Preference is given to using carriers which are, at least partially in the region of the positions with the immobilized receptors, optically transparent or/and electrically conductive.

The microfluidic carrier used for the method of the invention comprises an array having a plurality of different receptors, for example with at least 10 and, preferably at least 20, different receptors. The receptors are preferably constructed step by step in situ on or in the carrier by location- or/and time-specifically immobilizing receptor building blocks in the in each case predetermined positions.

Only a single receptor species or receptor sequence or a mixture of a plurality of different receptor species or receptor sequences can be immobilized or synthesized in one predetermined position. It is possible, for example, to use mixtures of receptor species which are specific for the same target molecule to be extracted, for example a set of different hybridization probes for extraction of a single particular target nucleic acid.

The method of the invention is particularly suitable for use as integrated synthesis analysis (ISA) method, i.e. a carrier can be prepared in situ according to particular guidelines and then be used for an extraction cycle. This may be followed, where appropriate, by further synthesis-extraction cycles in analogy to the ISA principle described in WO 00/13018. In this way it is possible to extract even very different molecules such as mRNA molecules or DNA sequences, using a carrier. In addition, it is possible by using a single carrier to change to new extraction targets. The method can be readily automated and be combined with further subsequent processing steps such as an amplification reaction, for example by using a PCR thermocycler, a detection or an in vitro translation. Said subsequent processing steps may make use of a common, integrated reaction carrier.

Apart from the actual synthesis/reaction areas, the carrier may also include other microfluidic functions or elements, such as, for example, additional reaction spaces, for example for enzyme reactions within the carrier, reservoirs, valves, pumps, thermoelements, reaction areas containing other immobilized biologically functional molecules, etc. Particular preference is given to the presence of devices for tempering the carrier, for example for setting a particular temperature or a particular temperature profile during the extraction process. The carrier comprises particularly preferably thermoelements, for example Peltier elements which enable the temperature on the carrier or on individual areas of the carrier to be set location- or/and time-specifically, for hybridizations and subsequent melting of nucleic acid double strands and for other temperature-dependent or temperature-controlled biochemical reactions. In addition, devices for modulated addition of buffers, for example from different reservoirs, may also be present, in order to modulate reaction conditions, for example hybridization conditions with respect to stringency, on the carrier or on areas of the carrier in a time- or/and location-specific manner.

Furthermore, the carrier may comprise additional functional biological molecules in immobilized form, for example polymeric probes which are used for analyzing the isolated target molecules, for example for quality control. Furthermore, functional biological molecules may be present in immobilized form for enzymic reactions, for example enzymes, PCR primers, ribozymes, etc., modifications or derivatizations of the target molecules.

In another embodiment, the carrier is integrated in an apparatus comprising a programmable light source matrix, a detector matrix, a carrier preferably arranged between light source matrix and detector matrix and also means for supplying fluids into the carrier and for discharging fluids from said carrier. The programmable light source matrix or illumination matrix may be a reflection matrix, a light valve matrix, for example an LCD matrix or a self-emitting illumination matrix. Light matrices of this kind are disclosed in WO 00/13017 and WO 00/13018. The detector matrix may, where appropriate, be integrated in the carrier body.

The in situ construction of receptors on the carrier may comprise fluidochemical steps, photochemical steps, electrochemical steps or combinations of two or more of said steps. An example of an electrochemical synthesis of receptors on a carrier is described in DE 101 20 633.1. An example of a hybrid method comprising the combination of fluidochemical steps and photochemical steps is described in DE 101 22 357.9.

The use of a carrier comprising an array having a multiplicity of different receptors makes it possible to immobilize a plurality of different target molecules of a complex sample in a single step. The target molecules immobilized on the carrier may likewise be eluted in a single step. However, preference is given to location- or/and time-specific elution, with a first step comprising first eluting individual target molecules or individual groups of target molecules from the carrier and one or more subsequent steps comprising the elution of further target molecules or groups of target molecules. This location- or/and time-specific elution preferably encompasses fluidochemical, photochemical or electrochemical steps or combinations thereof. Preference is likewise given to using local temperature changes on the carrier.

In a particularly preferred embodiment of the invention, elution is carried out by means of a location-specific change in temperature, for example a temperature increase resulting in denaturation of nucleic acid double strands. Such a location-specific change in temperature may be effected by location-specific thermoelements or/and location-resolved action of radiation, for example UV/VIS radiation and in particular IR radiation, which action results in location-specific evolution of heat.

Separate location- or/and time-specific elution of different target molecules may, where appropriate, also be achieved by separating individual reaction spaces from one another by means of hydrophobic barriers along channels, in order to avoid mixing of eluted target molecules, for example nucleic acids, due to diffusion.

Location- or/and time-specific elution may also specifically generate mixtures of selected target molecules, obtaining, for example, multiple fractions of target molecule mixtures. Furthermore, target molecule gradients or gradient mixtures may be prepared by different elution effect in different positions, for example by thermal effects of different lengths.

The method of the invention may also be used for isolating proteins and other molecules, in particular DNA-binding molecules, if suitable capture probes are selected as receptors. Therefore, in another preferred embodiment, DNA-binding proteins may be extracted with the aid of DNA capture probes which may be present in double- or single-stranded form. In yet another preferred embodiment, it is also possible to use peptide capture probes for isolating proteins or DNA molecules. In yet another preferred embodiment, the capture probes used are nucleic acids having special binding properties, for example aptamers or ribozymes.

Compared to the prior art, the method of the invention has the advantage of allowing selective isolation of a plurality of target molecules in a single operation. The use of microfluidic carriers makes it possible to use for this small sample volumes of, for example, from 0.1 µl to 100 µl. Despite these small sample volumes, high local target molecule concentrations are achieved in the carrier, making a very specific and comprehensive extraction possible.

Due to the microfluidic format, extraction does not cause any aerosol formation, and thus cross-contamination, as is the case, for example, in column-based methods with centrifugation step or vacuum suction. Moreover, there is no competition for uniform binding sites by nucleic acids occurring with different frequencies or/and present in a tertiary structure, which may otherwise proceed to the advantage of the more frequent or less-folded molecules, as is the case for poly-A columns. The nucleic acids selectively extracted by the method of the invention are therefore in subsequent steps such as, for example, PCR easier to manage than a mixture, thereby causing fewer problems, for example wrong primer binding, etc. Finally, the method of the invention may also be readily automated. In particular, it is possible to automatically connect processes occurring upstream or downstream, for example an enzymic reaction or storage of the isolated molecules in suitable containers.

An additional advantage of using microfluidic carriers as isolation matrix is the possibility of carrying out one or more cycles of binding and subsequent elution of target molecules according to the flow-through principle, with a cycle of this kind comprising the steps: binding, washing of unwanted molecules, eluting of the desired molecules and reconstituting of the carrier. Isolation may also take place with circulation of the target molecule mixture for improving active interactions between receptor and analyte or improving the washing process and reconstitution.

The extracted target molecules may be used directly or indirectly for diagnostic or therapeutic purposes. The extracted material may furthermore be used in subsequent reactions. Thus it is possible to generate from extracted nucleic acids proteins or peptides, for example by transfer into suitable vectors (cloning) or into suitable target cells (transformation or transfection) or by in vitro translation, in particular isolation of mRNA target molecules.

The course of the method is outlined below, using the example of nucleic acids as target molecules:

1. determination of data for the sequences of the target molecules to be extracted from a sample, for example 20 genes of a model organism which is studied at the time; with at least partially known sequences of said 20 genes;
2. determination of suitable capture probes complimentary to unique regions in the selected genes, preferably with the aid of a computer algorithm;
3. preparation of the sample by isolating total RNA from cells of the model organism;
4. providing an apparatus for in situ synthesis of appropriate capture probes in or on a microfluidic reaction carrier;
5. entering the determined capture probe sequence into a synthesis control unit which may be integrated with the microfluidic carrier;
6. synthesizing the selected capture probe sequence in or on the microfluidic reaction carrier;
7. adding the sample so that said sample is washed into the channels of the reaction carrier;

8. equilibrating the conditions on the carrier so as to enable target molecules and capture probes to bind to one another (hybridization) under suitable buffer conditions and a suitable temperature;
9. flushing the channels in order to remove unbound material;
10. changing the buffer (stringency) and possibly the temperature to destroy the specific hybrids between target molecules and capture probes;
11. specifically flushing out and collecting the detached target molecules;
12. further use of the selectively extracted nucleic acids, for example in PCR and cloning, in order to study then, after expression, the effect of the gene products.

The above-described principle may also be used in a modified form for selectively removing particular components (preferably more than one species) from a sample containing a target molecule or a mixture of target molecules. Interfering components may be removed, for example repetitive elements or telomer sequences when analyzing gene fragments; filtering out particular genes (e.g. housekeeping genes) in transcription analyses; protein or protein classes interfering with the proteome analysis of (rare) proteins. Thus it is possible to capture known components and to elute only desired, for example known or unknown, target molecules, thereby concentrating desired nucleic acids or proteins or other desired biomolecules.

In this kind of embodiment, the method proceeds as follows:
1. determination of data for the sequences of interfering components;
2. determination of suitable capture probes for interfering components;
3.-7. as above;
8. equilibrating under conditions under which interfering components bind;
9. specifically flushing out and collecting the desired molecules (interfering elements remain on the carrier).

This procedure decreases the concentration of interfering components, thus enabling the desired molecules subsequently to be analyzed with higher precision. Furthermore, the desired target molecules of the sample to be studied are concentrated and interfering molecules, for example multiple species in parallel, may be specifically removed from the molecule mixture.

Thus the invention further relates to a method for isolating target molecules from a sample, comprising the following steps:
(a) providing a microfluidic carrier having an array of a plurality of different receptors which are immobilized on or in the carrier on in each case different positions,
(b) directing a sample comprising target molecules to be isolated through said microfluidic carrier under conditions under which interfering molecules can specifically bind to the receptors immobilized on the carrier, and
(c) eluting the unbound target molecules from the carrier.

In this embodiment, the method is conducted according to the illustration of the first embodiment, with the proviso that the target molecules present in the sample do not bind or bind to a lesser extent than the interfering components to the receptors on the carrier.

Finally, the present invention also comprises an embodiment relating to a method for isolating target molecules from a sample, which method comprises combining at least one process cycle in which the target molecules bind to the receptors and at least one process cycle in which no or only a few target molecules bind to the receptors. Preference is given to carrying out first a process cycle in which no or only a few target molecules bind and which is followed by a process cycle in which the target molecules bind and are then eluted from the carrier in a location- or/and time-specific manner.

Furthermore, the following figures are intended to illustrate the invention in more detail.

FIG. 2 depicts the specific hybridization of nucleic acid target molecules to a microfluidic reaction carrier and their quantitative extractability.

Figure 1:
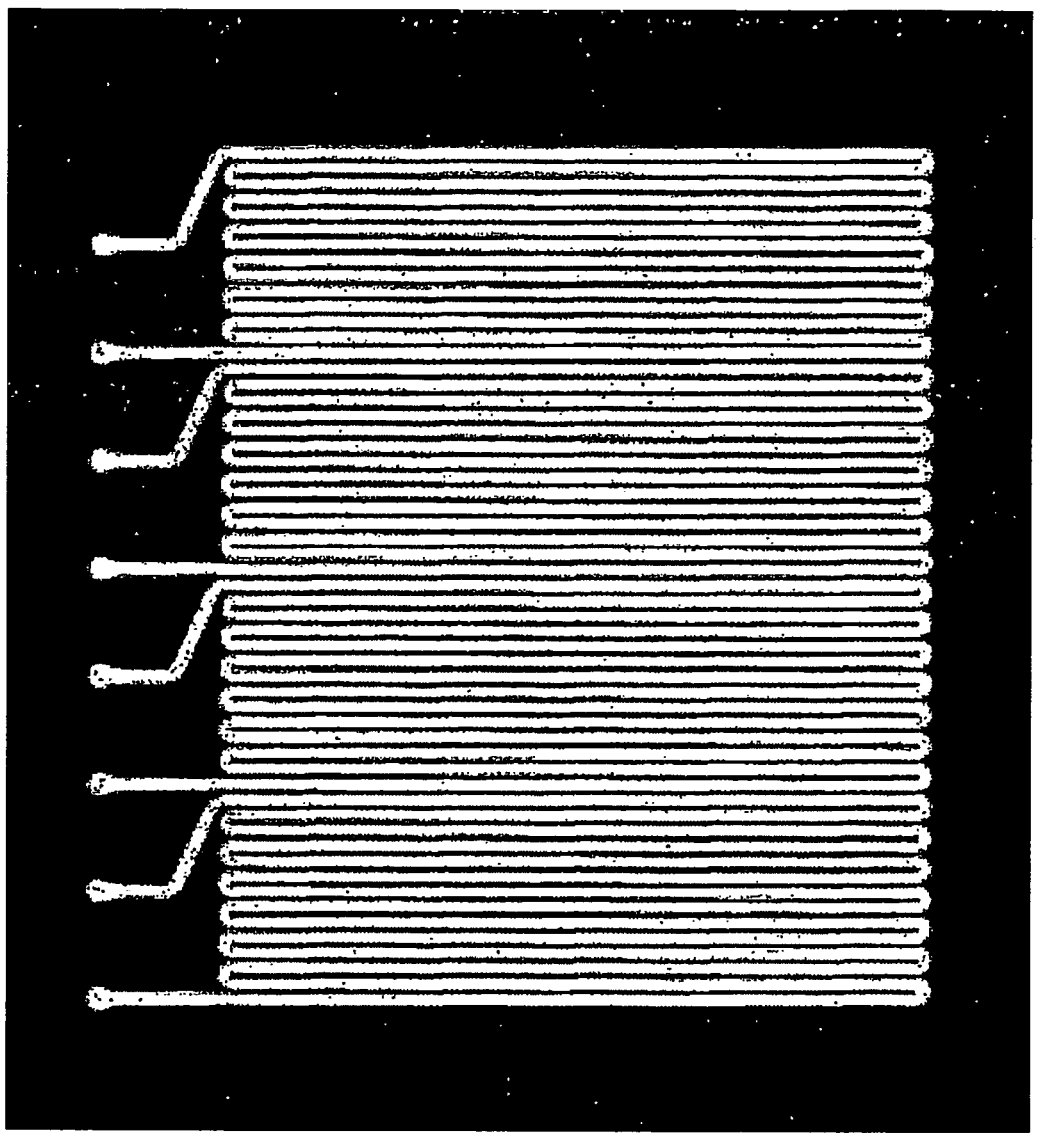
FIG. 1 depicts an example of a suitable microfluidic reaction carrier having 4 separate channels in total.

FIG. 2A indicates the hybridization of a target molecule to predetermined positions on a microfluidic reaction carrier.

FIG. 2B depicts the carrier after extraction and indicates that quantitative elution of the target molecule has taken place.

The invention claimed is:

1. A method for selectively isolating, in parallel, a plurality species of target molecules from a sample, comprising the steps:
(a) providing a microfluidic carrier having an array of a plurality of different receptors which are immobilized on or in the carrier wherein each different receptor is immobilized at a different position,
(b) directing a sample comprising target molecules to be selectively isolated in parallel through said microfluidic carrier under conditions under which said target molecules can specifically bind to the receptors immobilized on the carrier,
(c) removing unbound material of the sample from the carrier, and
(d) isolating, in parallel, the target molecules bound to the carrier by selective elution of said species of target molecules.

2. The method as claimed in claim 1, wherein said target molecules are selected from the group consisting of nucleic acids, polypeptides, peptides and saccharides.

3. The method as claimed in claim 1, wherein said target molecules are selected from the group consisting of nucleic acids.

4. The method as claimed in claim 3, wherein said receptors used are hybridization probes.

5. The method as claimed in claim 4, wherein said hybridization probes used are selected from the group consisting of nucleic acids and nucleic acid analogs.

6. The method as claimed in claim 4, wherein the length of said hybridization probes corresponds to 10-100 nucleotides.

7. The method as claimed in claim 1, wherein said sample is selected from the group consisting of a sample of biological origin, synthetic origin and both biological and synthetic origin.

8. The method as claimed in claim 1, wherein said sample has been subjected to one or more pretreatment steps.

9. The method as claimed in claim 1, wherein said microfluidic carrier comprises closed channels.

10. The method as claimed in claim 9, wherein said carrier has microchannels of 10-1000 µm in diameter.

11. The method as claimed in claim 1, wherein said array on the carrier comprises at least 10 positions with different receptors.

12. The method as claimed in claim 11, wherein the receptors in said positions are selected from the group consisting of individual sequences, individual sequence mixtures and both.

13. The method as claimed in claim 1, wherein said receptors of the array are constructed in situ on or in the carrier by stepwise immobilizing receptor building blocks in each position, wherein said position is predetermined and wherein said immobilizing is location-specific, time-specific or both.

14. The method as claimed in claim 13, wherein the cycle comprising in situ construction of the receptors and steps (a) to d) is repeated one or more times.

15. The method as claimed in claim 13, wherein said carrier is used together with a programmable light source matrix and a detection matrix.

16. The method as claimed in claim 1, wherein said elution of target molecules bound to the carrier is performed in a location-specific manner, a time-specific manner or both.

17. The method as claimed in claim 16, wherein said elution of target molecules bound to the carrier comprises a method selected from the group consisting of fluidochemical, photochemical, electrochemical methods and combinations thereof.

18. The method as claimed in claim 17, wherein said receptors are light-sensitive.

19. The method as claimed in claim 16, wherein said elution comprises changing the temperature on the carrier in a location-specific manner, a time-specific manner or both.

20. The method as claimed in claim 19, wherein said carrier comprises integrated thermoelements.

21. The method as claimed in claim 1, further comprising subjecting said eluted target molecules to a subsequent reaction.

22. The method as claimed in claim 1, further comprising using said eluted target molecules directly or indirectly for diagnostic or therapeutic purposes.

23. The method as claimed in claim 1, wherein said carrier includes additional functional biological molecules in immobilized form.

24. The method as claimed in claim 23, wherein said additional functional biological molecules are polymeric probes and are used for analyzing the isolated target molecules.

25. A method for selectively isolating in parallel, several species of target molecules from a sample, comprising the steps:
(a) providing a microfluidic carrier having an array of a plurality of different receptors which are immobilized on or in the carrier wherein each different receptor is immobilized at a different position,
(b) directing a sample comprising target molecules to be selectively isolated in parallel through said microfluidic carrier under conditions under which interfering components of a sample can specifically bind to the receptors immobilized on the carrier, and
(c) isolating the unbound target molecules from the carrier by elution.

26. The method as claimed in claim 3, wherein said nucleic acids comprise DNA molecules.

27. The method as claimed in claim 3, wherein said nucleic acids comprise RNA molecules.

28. The method as claimed in claim 11, wherein said array on the carrier comprises at least 20 positions with different receptors.

29. A method for selectively isolating, in parallel, a plurality species of target molecules from a sample, comprising the steps:
(a) providing a microfluidic carrier,
(b) synthesizing in situ on said microfluidic carrier an array of a plurality of different receptors, immobilized on or in the carrier, wherein each different receptor is immobilized at a different position,
(c) directing a sample comprising target molecules to be selectively isolated in parallel through said microfluidic carrier under conditions under which said target molecules can specifically bind to the receptors immobilized on the carrier,
(d) removing unbound material of the sample from the carrier, and
(e) isolating, in parallel, the target molecules bound to the carrier by selective elution of said species of target molecules.

30. A method for isolating nucleic acid analytes comprising the steps:
(a) providing a microfluidic carrier,
(b) synthesizing in situ on said microfluidic carrier an array of a plurality of different receptors, immobilized on or in the carrier, wherein each different receptor is immobilized at a different position,
(c) directing a sample comprising target molecules to be selectively isolated in parallel through said microfluidic carrier under conditions under which said target molecules can specifically bind to the receptors immobilized on the carrier,
(d) removing unbound material of the sample from the carrier, and
(e) isolating, in parallel, the target molecules bound to the carrier by selective elution of said species of target molecules.

* * * * *